(12) United States Patent
Allen et al.

(10) Patent No.: US 11,241,340 B2
(45) Date of Patent: Feb. 8, 2022

(54) ASSISTIVE DEVICE FOR HAMSTRING INJURY REHABILITATION

(71) Applicant: The Board of Trustees of The University of Alabama, Tuscaloosa, AL (US)

(72) Inventors: Jeff Allen, Northport, AL (US); Clay Keith, Tuscaloosa, AL (US); Tim Haskew, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 303 days.

(21) Appl. No.: 16/534,355

(22) Filed: Aug. 7, 2019

(65) Prior Publication Data
US 2020/0046571 A1     Feb. 13, 2020

Related U.S. Application Data

(60) Provisional application No. 62/716,052, filed on Aug. 8, 2018.

(51) Int. Cl.
*A61F 13/00*     (2006.01)
*A61F 13/06*     (2006.01)

(52) U.S. Cl.
CPC .................................. *A61F 13/06* (2013.01)

(58) Field of Classification Search
CPC .. A61F 13/06; A61F 5/02; A61F 5/022; A61F 5/024; A63B 21/0552; A63B 21/4025
See application file for complete search history.

(56) References Cited

U.S. PATENT DOCUMENTS

| | | | | |
|---|---|---|---|---|
| 5,203,754 A | * | 4/1993 | Maclean | A63B 21/0004 482/121 |
| 5,286,251 A | * | 2/1994 | Thompson | A61F 5/3715 128/100.1 |
| 5,960,474 A | * | 10/1999 | Dicker | A42B 3/0406 2/69 |
| 5,993,362 A | * | 11/1999 | Ghobadi | A63B 21/0004 482/121 |
| 6,179,760 B1 | * | 1/2001 | Rumbaugh | A63B 21/4025 482/121 |
| D457,965 S | * | 5/2002 | Firer | A63B 21/0442 D24/190 |

(Continued)

*Primary Examiner* — Kim M Lewis
(74) *Attorney, Agent, or Firm* — Meunier Carlin & Curfman LLC

(57) ABSTRACT

Various implementations include an assistive hamstring device including a belt, knee sleeve, first elastic strap, second elastic strap, and third elastic strap. The first elastic strap extends between a first dorsal belt portion of the belt located adjacent a sagittal plane on a dorsal side of the person and a lateral knee portion of the knee sleeve located adjacent a lateral side of the knee. The second elastic strap extends between a side belt portion of the belt located adjacent a coronal plane of the person and a medial knee portion of the knee sleeve located adjacent a medial side of the knee. The third elastic strap extends between a second dorsal belt portion of the belt located between the first and side belt portion and an intermediate dorsal knee portion of the knee sleeve located between the lateral and medial knee portion, along the dorsal portion of the knee.

23 Claims, 5 Drawing Sheets

(56) References Cited

U.S. PATENT DOCUMENTS

| | | | |
|---|---|---|---|
| 6,428,495 B1 * | 8/2002 | Lynott | A61F 5/3715 128/875 |
| 6,837,834 B2 * | 1/2005 | Basting | A63B 21/0552 482/121 |
| 7,744,511 B2 * | 6/2010 | Grigoriev | A63B 21/4011 482/124 |
| 7,931,571 B2 * | 4/2011 | Bernardoni | A61F 5/0102 482/124 |
| 8,968,166 B2 * | 3/2015 | Cranke | A63B 21/0442 482/124 |
| 10,195,475 B2 * | 2/2019 | Schreiber | A63B 21/0552 |
| 10,758,771 B1 * | 9/2020 | Cranke | A63B 21/00185 |
| 2015/0196789 A1 | 7/2015 | Whitt | |

* cited by examiner

ASSISTIVE DEVICE FOR HAMSTRING INJURY REHABILITATION

CROSS REFERENCE TO RELATED APPLICATION

This application claims the benefit of U.S. Provisional Application No. 62/716,052, entitled "Assistive Device for Hamstring Injury Rehabilitation," filed Aug. 8, 2018, the content of which is herein incorporated by reference in its entirety.

BACKGROUND

The hamstring is comprised of three muscles: the semitendinosus, the semimembranosus, and the biceps femoris. These three hamstring muscles cross both the hip and the knee joint and are involved in knee flexion and hip extension.

Hamstring strain is one of the most common and prevalent musculoskeletal injuries in the world due to the hamstring's complex use during gait. Traditional rehabilitation for hamstring injury involves wrapping the entire thigh with an elastic wrap to provide compression and increase blood flow. However, this technique does not reduce stress when the hamstring contracts. Furthermore, the tension of the wrap is perpendicular to hamstring tension. Thus, a need exists for a device and method for assisting hamstring injury rehabilitation that reduces stress when an injured hamstring contracts and provides tension in the direction of the hamstring tension.

BRIEF SUMMARY

Various implementations include an assistive hamstring device that includes a belt for being disposed around a waist and/or hips of a person, a knee sleeve for being disposed around a knee of the person, a first elastic strap having a first end portion and a second end portion, a second elastic strap having a first end portion and a second end portion, and a third elastic strap having a first end portion, a second end portion, and an intermediate portion between the end portions and spaced apart from at least the first end portion. The belt has a first dorsal belt portion for being disposed adjacent a sagittal plane on a dorsal side of the person, a side belt portion for being disposed adjacent a coronal plane of the person, and a second dorsal belt portion disposed between the first dorsal belt portion and the side belt portion, the second dorsal belt portion for being disposed adjacent the dorsal side of the person. The knee sleeve has a lateral knee portion for being disposed adjacent a lateral side of the knee, a medial knee portion for being disposed adjacent a medial side of the knee, and an intermediate dorsal knee portion for being disposed adjacent a dorsal portion of the knee between the lateral knee portion and the medial knee portion. The first end portion of the first elastic strap is coupled to the first dorsal belt portion, and the second end portion of the first elastic strap is coupled to the lateral knee portion. The first end portion of the second elastic strap is coupled to the side belt portion, and the second end portion of the second elastic strap is coupled to the medial knee portion. And, the first end portion of the third elastic strap is coupled to the second dorsal belt portion, and the intermediate portion of the third elastic strap is coupled to the intermediate dorsal knee portion.

In some implementations, the first, second, and third elastic straps include nylon.

In some implementations, the device includes an ankle sleeve for being disposed around an ankle of the person. The second end portion of the third elastic strap is coupled to the ankle sleeve.

In some implementations, the intermediate portion and the second end portion of the third elastic strap are adjacent, and the second end portion of the third elastic strap is also coupled to the intermediate dorsal knee portion.

In some implementations, the device includes a fourth strap having a first end portion coupled to the belt and a second end portion opposite the first end portion. The second end portion is for being coupled to a shoulder support for being disposed on a shoulder of the person. In some implementations, the shoulder support includes shoulder pads to be worn by the person.

In some implementations, the device includes at least one shoulder strap that extends over a shoulder of the person. The shoulder strap includes a first end portion and a second end portion, and the first and second end portions are coupled to the belt. In some implementations, a first end portion of the shoulder strap is coupled to the dorsal portion of the belt and a second end portion of the shoulder strap is coupled to a frontal portion of the belt.

In some implementations, the device includes a pair of tights. The tights include the belt and the knee sleeve. At least a portion of each strap is coupled to the tights. In some implementations, the straps are disposed within one or more sleeves defined by the tights. The one or more sleeves extend between the belt and the knee sleeve of the tights. In some implementations, the end portions of the straps are sewn to the tights.

According to various other implementations, a method of assisting hamstring injury recovery includes: (1) disposing a belt around a waist and/or hips of a person, the belt having a first dorsal belt portion disposed adjacent a sagittal plane on a dorsal side of the person, a side belt portion disposed adjacent a coronal plane of the person, and a second dorsal belt portion disposed between the first dorsal belt portion and the side belt portion, the second dorsal belt portion disposed adjacent the dorsal side of the person; (2) disposing a knee sleeve around a knee of the person, the knee sleeve having a lateral knee portion disposed adjacent a lateral side of the knee, a medial knee portion disposed adjacent a medial side of the knee, and a middle dorsal knee portion disposed adjacent a dorsal portion of the knee between the lateral knee portion and the medial knee portion; (3) coupling a first end portion of a first elastic strap to the first dorsal belt portion and a second end portion of the first elastic strap to the lateral knee portion; (4) coupling a first end portion of a second elastic strap to the side belt portion and a second end portion of the second elastic to the medial knee portion; and (5) coupling a first end portion of a third elastic strap to the second dorsal belt portion and an intermediate portion of the third elastic strap to the intermediate dorsal knee portion, wherein the intermediate portion of the third elastic strap is spaced apart from the first end portion of the third elastic strap and is between the first and second end portion of the third elastic strap.

In some implementations, the first, second, and third elastic straps include nylon.

In some implementations, the method includes disposing an ankle sleeve around an ankle of the person. The second end portion of the third elastic strap is coupled to the ankle sleeve.

In some implementations, the intermediate portion and the second end portion of the third elastic strap are adjacent each other, and the second end portion of the third elastic strap is also coupled to the knee sleeve.

In some implementations, the method includes coupling a first end portion of a fourth strap to the belt and a second end portion of the fourth strap to a shoulder support disposed on a shoulder of the person. In some implementations, the shoulder support includes shoulder pads worn by the person.

In some implementations, the method includes disposing at least one shoulder strap over a shoulder of the person. The shoulder strap has a first end portion and second end portion, and the first and second end portions of the shoulder strap are coupled to the belt. In some implementations, the first end portion of the shoulder strap is coupled to the dorsal portion of the belt and the second end portion of the shoulder strap is coupled to a frontal portion of the belt.

In some implementations, disposing the belt around the waist and/or hips and disposing the knee sleeve around the knee includes donning a pair of tights into which the belt and knee sleeve are incorporated and to which at least a portion of the straps are coupled. In some implementations, the tights define one or more sleeves and the straps are disposed within the one or more sleeves. In some implementations, coupling end portions of the straps to the tights includes sewing the end portions of the straps to the tights.

In some implementations, coupling respective end portions of the first, second, and third straps to the belt includes sewing the respective end portions of the first, second, and third straps to the belt, and coupling respective end portions of the first and second straps to the knee sleeve includes sewing the respective end portions of the first and second straps to the knee sleeve.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

Figure 1:
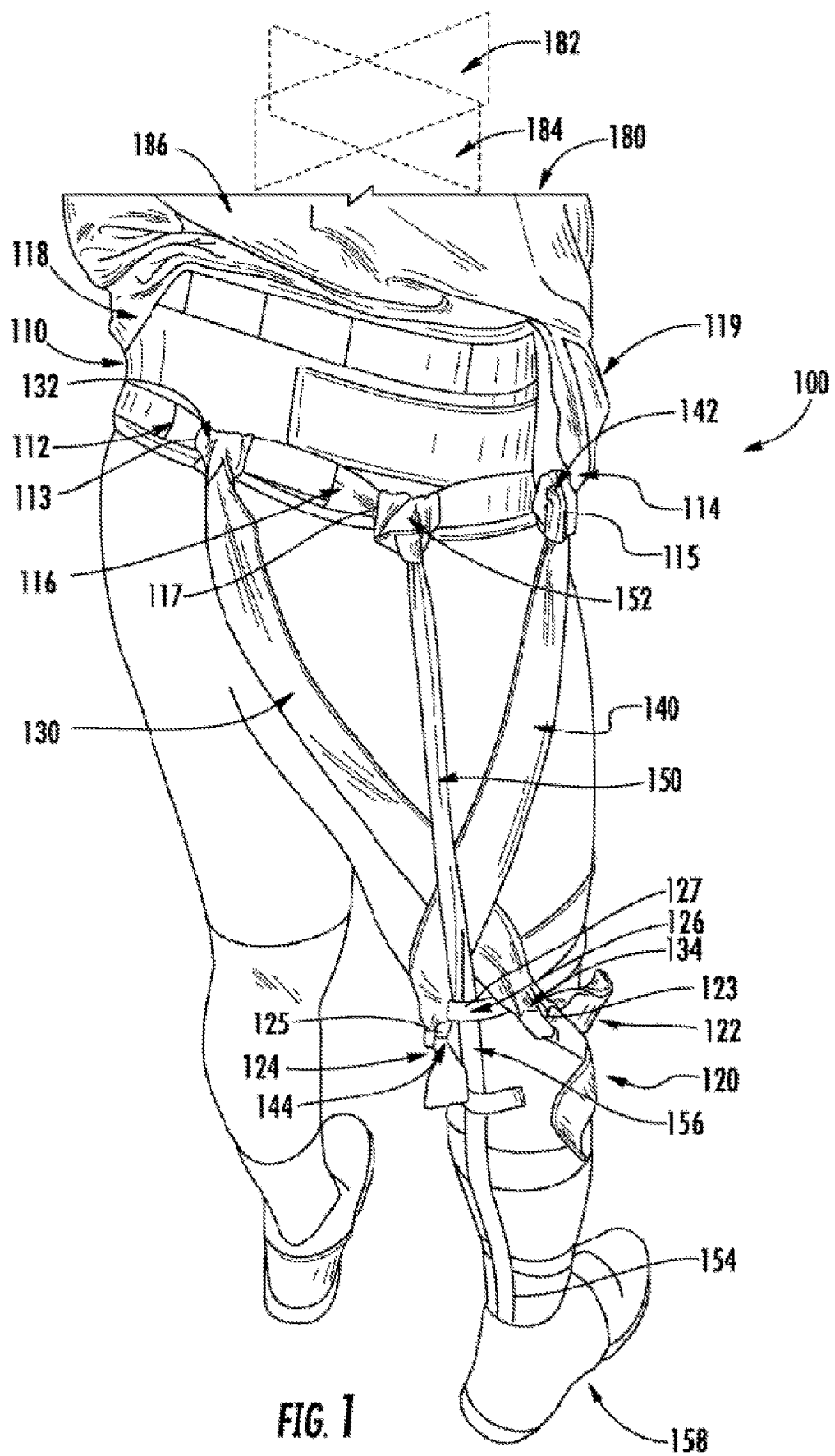
FIG. 1 is a perspective view of an assistive device for hamstring injury rehabilitation in accordance with one implementation.

Various implementations include an assistive hamstring device that includes a belt for being disposed around a waist and/or hips of a person, a knee sleeve for being disposed around a knee of the person, a first elastic strap having a first end portion and a second end portion, a second elastic strap having a first end portion and a second end portion, and a third elastic strap having a first end portion, a second end portion, and an intermediate portion between the end portions and spaced apart from at least the first end portion. The belt has a first dorsal belt portion for being disposed adjacent a sagittal plane on a dorsal side of the person, a side belt portion for being disposed adjacent a coronal plane of the person, and a second dorsal belt portion disposed between the first dorsal belt portion and the side belt portion, the second dorsal belt portion for being disposed adjacent the dorsal side of the person. The knee sleeve has a lateral knee portion for being disposed adjacent a lateral side of the knee, a medial knee portion for being disposed adjacent a medial side of the knee, and an intermediate dorsal knee portion for being disposed adjacent a dorsal portion of the knee between the lateral knee portion and the medial knee portion. The first end portion of the first elastic strap is coupled to the first dorsal belt portion, and the second end portion of the first elastic strap is coupled to the lateral knee portion. The first end portion of the second elastic strap is coupled to the side belt portion, and the second end portion of the second elastic strap is coupled to the medial knee portion. And, the first end portion of the third elastic strap is coupled to the second dorsal belt portion, and the intermediate portion of the third elastic strap is coupled to the intermediate dorsal knee portion.

According to various other implementations, a method of assisting hamstring injury recovery includes: (1) disposing a belt around a waist and/or hips of a person, the belt having a first dorsal belt portion disposed adjacent a sagittal plane on a dorsal side of the person, a side belt portion disposed adjacent a coronal plane of the person, and a second dorsal belt portion disposed between the first dorsal belt portion and the side belt portion, the second dorsal belt portion disposed adjacent the dorsal side of the person; (2) disposing a knee sleeve around a knee of the person, the knee sleeve having a lateral knee portion disposed adjacent a lateral side of the knee, a medial knee portion disposed adjacent a medial side of the knee, and a middle dorsal knee portion disposed adjacent a dorsal portion of the knee between the lateral knee portion and the medial knee portion; (3) coupling a first end portion of a first elastic strap to the first dorsal belt portion and a second end portion of the first elastic strap to the lateral knee portion; (4) coupling a first end portion of a second elastic strap to the side belt portion and a second end portion of the second elastic to the medial knee portion; and (5) coupling a first end portion of a third elastic strap to the second dorsal belt portion and an intermediate portion of the third elastic strap to the intermediate dorsal knee portion, wherein the intermediate portion of the third elastic strap is spaced apart from the first end portion of the third elastic strap and is between the first and second end portion of the third elastic strap.

Taken together, the three straps mimic the angles and forces associated with the hamstring, thus reducing the contractive force of the actual muscles during concentric movement, according to some implementations. During eccentric motion, the quadriceps muscle group is used to extend the straps. This arrangement reduces muscle stress on the hamstring and thus speeds recovery from hamstring injury.

Implementations of the devices and methods can be used in the physical therapy equipment market and the athletic equipment and recovery market. For example, they can be used by athletes or non-athletes, such as workers, with hamstring injuries to reduce the risk of worsening the injury and to accelerate recovery from the injury.

Figure 2:
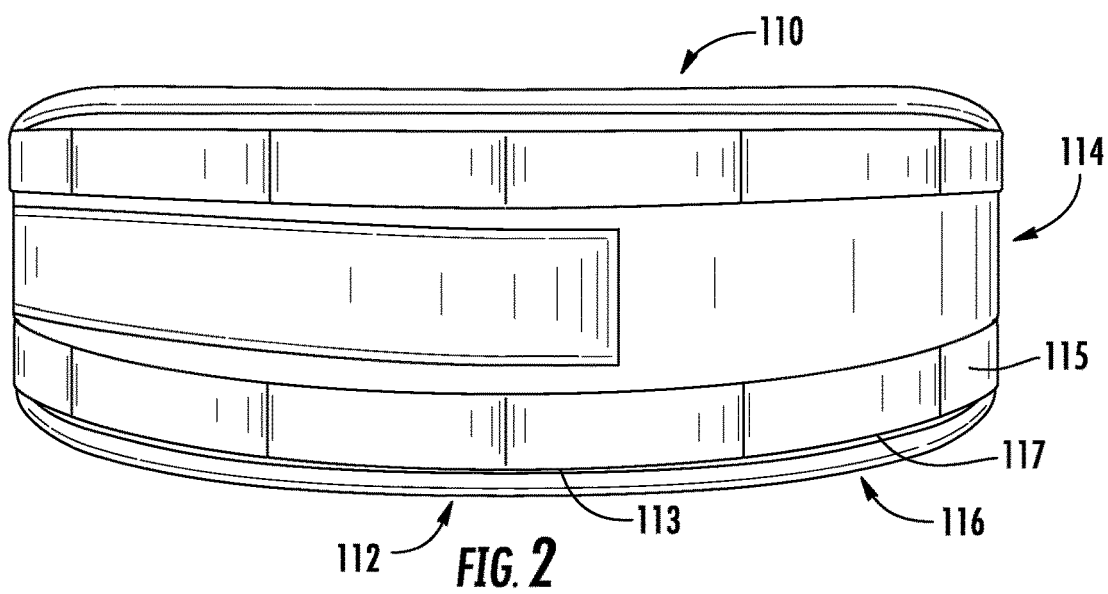
FIG. 2 is a perspective view of the belt for the assistive device for hamstring injury rehabilitation of FIG. 1.

FIG. 1 shows one implementation of an assistive hamstring device 100 including a belt 110, a knee sleeve 120, a first elastic strap 130, a second elastic strap 140, and a third elastic strap 150. As shown in FIGS. 1 and 2, the belt 110 has a first dorsal belt portion 112, a side belt portion 114, and a second dorsal belt portion 116. When disposed around a waist and/or hips of a person 180, the first dorsal belt portion 112 is positioned such that it is located adjacent a sagittal plane 182 on a dorsal side 186 of the person 180. The side belt portion 114 is located adjacent a coronal plane 184 of the person 180. The second dorsal belt portion 116 is located between the first dorsal belt 112 portion and the side belt portion 114, along the dorsal side 186 of the person 180. Each of the first dorsal belt portion 112, side belt portion 114, and second dorsal belt portion 116 have coupling portions 113, 115, 117, respectively, for coupling elastic straps 130, 140, 150, as shown in FIG. 1 and described further below.

Figure 3:
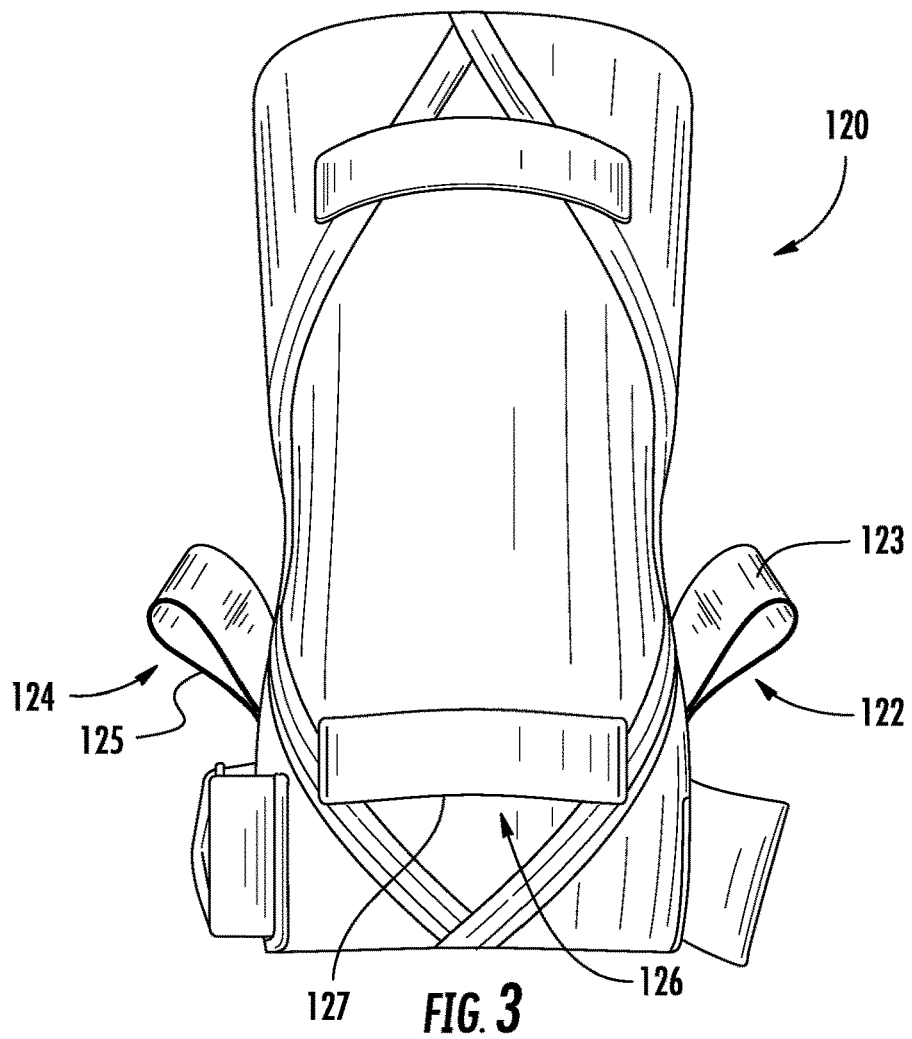
FIG. 3 is a perspective view of the knee sleeve for the assistive device for hamstring injury rehabilitation of FIG. 1.

As shown in FIGS. 1 and 3, the knee sleeve 120 has a lateral knee portion 122, a medial knee portion 124, and an intermediate dorsal knee portion 126. When disposed around a knee of the person 180, the lateral knee portion 122 is adjacent a lateral side of the knee 192. The medial knee portion 124 is adjacent a medial side of the knee 194. The intermediate dorsal knee portion 126 is between the lateral knee portion 122 and the medial knee portion 124, along the dorsal portion of the knee. Each of the lateral knee portion 122, medial knee portion 124, and intermediate dorsal knee portion 126 have coupling portions 123, 125, 127, respectively, for coupling elastic straps 130, 140, 150, respectively, as shown in FIGS. 1 and 2 and described further below.

The elastic straps 130, 14, 150 couple the belt 110 and the knee sleeve 120. Each of the first 130, second 140, and third elastic straps 150 can be made of a material having sufficient elasticity to mimic the tension of the hamstring muscles in the directions of the hamstring muscles during eccentric motion and reduce stress on the hamstring muscles during concentric motion. The elastic straps may have a resistive force at 100% elongation of up to 25 lbs. For example, the resistive force of the elastic straps at 100% elongation is in the range of 3 to 15 lbs. For example, the straps may be made of nylon or rubber.

The first elastic strap 130 has a first end portion 132 and a second end portion 134. The first end portion 132 of the first elastic strap 130 is coupled to the coupling portion 113 of the first dorsal belt portion 112 of the belt 110, while the second end portion 134 of the first elastic strap 130 is coupled to the coupling portion 123 of the lateral knee portion 122 for the knee sleeve 120.

Similar to the first elastic strap 130, the second elastic strap 140 has a first end portion 142 and a second end portion 144. The first end portion 142 of the second elastic strap 140 is coupled to the coupling portion 115 of the side belt portion 114 of the belt 110, and the second end portion 144 of the second elastic strap 140 is coupled to the coupling portion 125 of the medial knee portion 124 of the knee sleeve 120.

The third elastic strap 150 also has a first end portion 152 and a second end portion 154, but also has an intermediate portion 156 between the end portions 152, 154. The first end portion 152 of the third elastic strap 150 is coupled to the coupling portion 117 of the second dorsal belt portion 116 of the belt 110, and the intermediate portion 156 of the third elastic strap 150 is coupled to the coupling portion 127 of the intermediate dorsal knee portion 126 of the knee sleeve 120.

In addition, the assistive hamstring device 100 includes an ankle sleeve 158 to be worn around the ankle 198 of the person 180. The third elastic strap 150 extends beyond the knee sleeve 120, and the second end portion 154 of the third elastic strap 150 is coupled to the ankle sleeve 198. However, in some implementations, no ankle sleeve 158 is used, and the intermediate portion 156 and the second end portion 154 of the third elastic strap 150 are adjacent each other such that the second end portion 154 of the third elastic strap 150 is also coupled to the knee sleeve 120.

Thus, the elastic straps 130, 140, 150 cross each other along the dorsal side 186 of the person's thigh as the elastic straps 130, 140, 150 extend from the belt 110 to the knee sleeve 120. This crossing of the elastic straps 130, 140, 150 mimics the angles of the hamstring muscles relative to each other.

In FIG. 1, the straps 130, 140 are tied to the belt 110 and the knee sleeve 120, and the strap 150 is tied to the belt 110 and the ankle sleeve 158. However, in other implementations, the straps 130, 140, 150 can be coupled to the belt 110, knee sleeve 120, and/or ankle sleeve 158 by any suitable fastening mechanism, including for example, fasteners (e.g., clips, buckles, snaps, hook and loop, etc.), adhesive, sewing, and/or sleeves or loops incorporated into the fabric of tights.

To use the assistive hamstring device 100 shown in FIGS. 1-3, the belt 110 is disposed around the waist and/or hips the person 180, the knee sleeve 120 is disposed around the person's knee, and the ankle sleeve 158 is disposed around the person's ankle. Each of the straps 130, 140, 150 are then coupled to the belt 110 and knee sleeve 120 as described above, and the second end portion 154 of the third strap 150 is coupled to the ankle sleeve 158. In this way, the straps 130, 140, 150 extend from the belt 110, across the dorsal side of the thigh of the person 180, to the knee sleeve 120, and the third elastic strap 150 extends beyond the knee sleeve 120 to the ankle of the person 180. In implementations that do not include the ankle sleeve 158, the second end portion 154 of the third strap 150 is coupled to the knee sleeve 120

Figure 5:
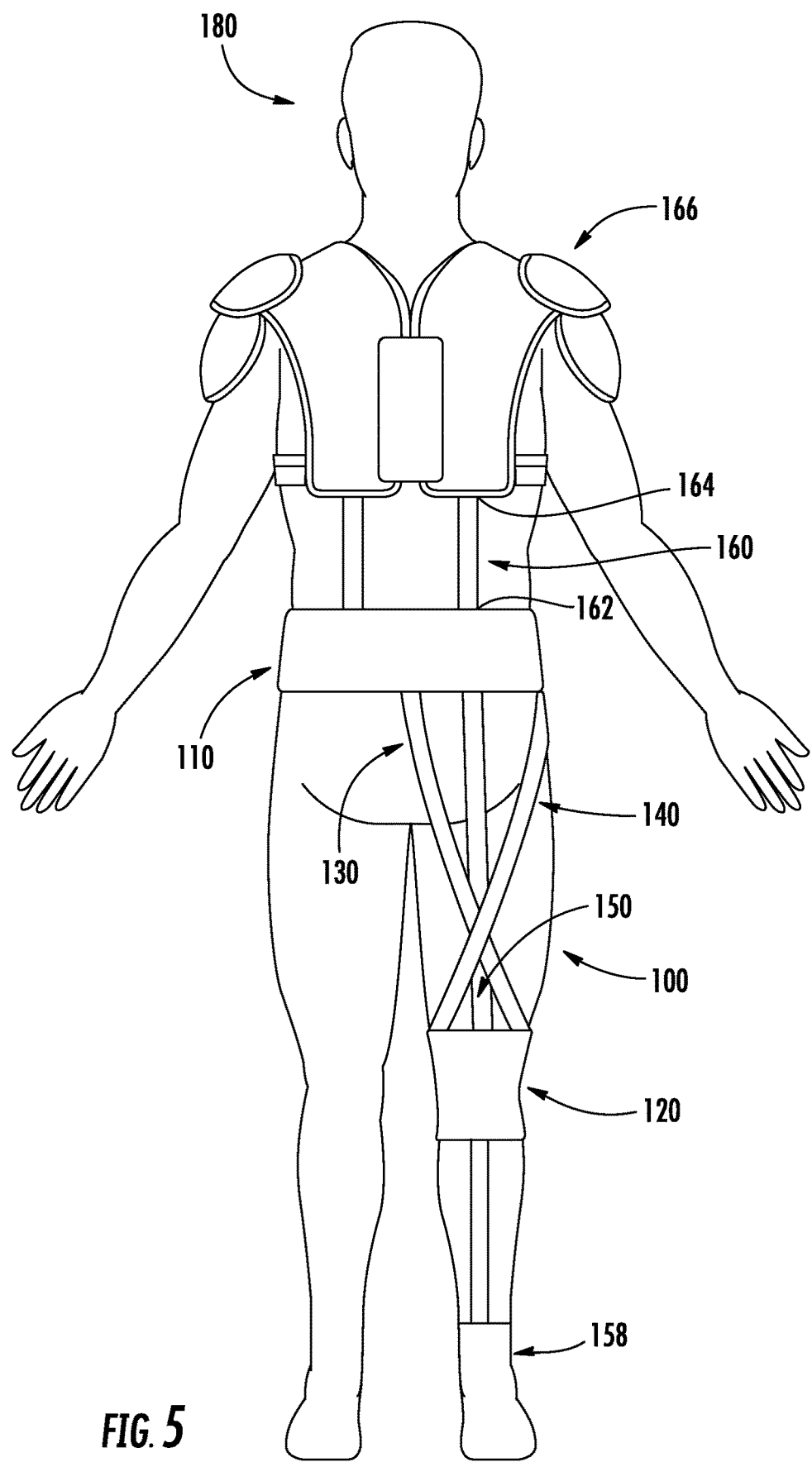
FIG. 5 is a perspective view of the assistive device for hamstring injury rehabilitation of FIG. 1 with a fourth elastic strap and shoulder pads.

FIG. 5 shows a further implementation of the assistive hamstring device 100 of FIG. 1. In this further implementation, the device 100 also includes a fourth strap 160 and a shoulder support 166 (e.g., shoulder pads worn by football players). The fourth strap 160 has a first end portion 162 and a second end portion 164. The first end portion 162 of the fourth strap 160 is coupled to the belt 110 and the second end portion 164 is coupled to the shoulder support 166. In use, the person 180 wears the shoulder support 166 on the person's shoulder, and the fourth strap 160 and shoulder support 166 prevent the belt 110 from being pulled downwardly by the straps 130, 140, 150.

Figure 6:
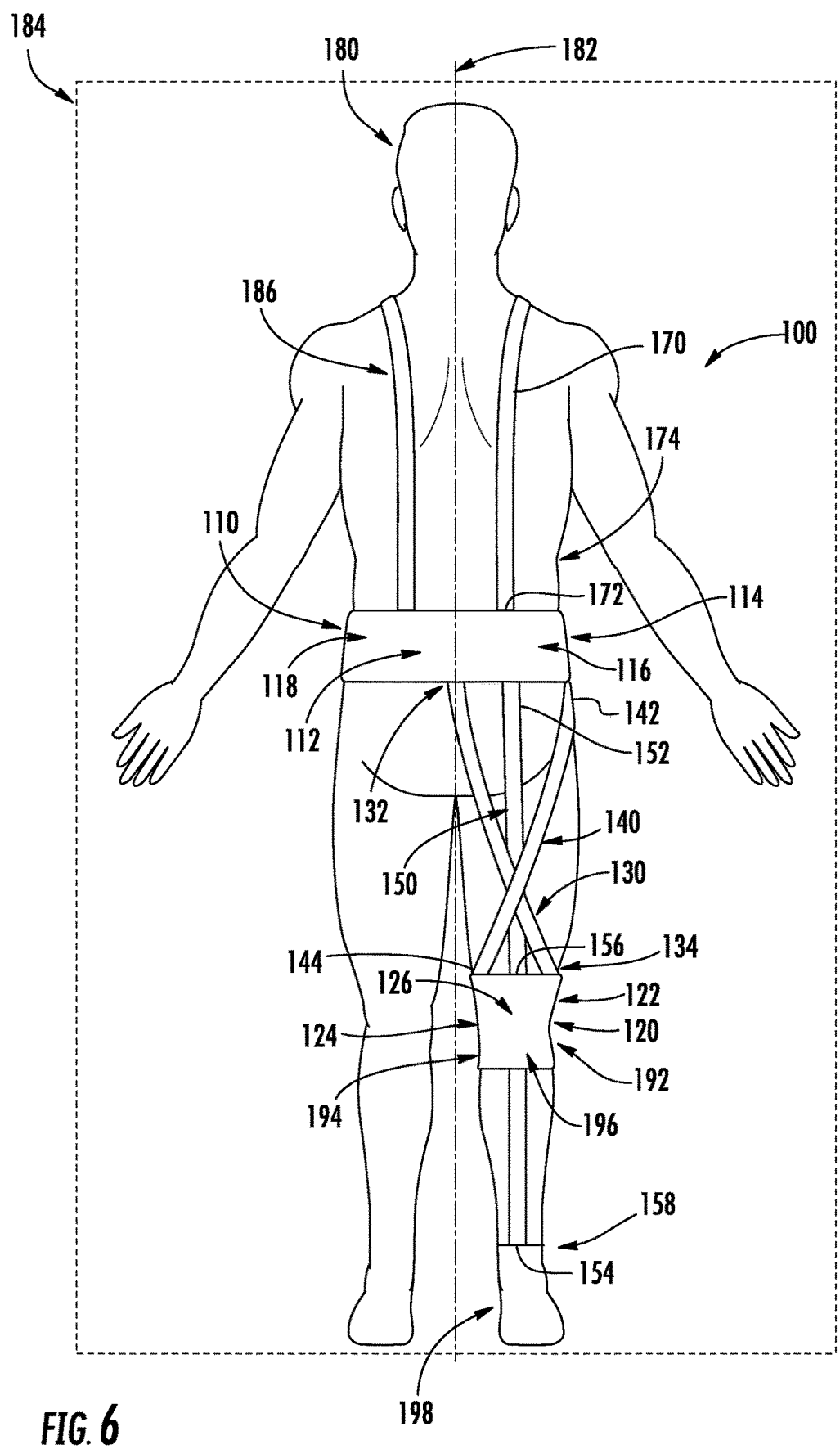
FIG. 6 is a perspective view of the assistive device for hamstring injury rehabilitation of FIG. 1 with a shoulder strap.

FIG. 6 shows another further implementation of the assistive hamstring device 100 of FIG. 1. In this further implementation, the device 100 includes one or more shoulder straps 170 that extend over a respective shoulder of the person 180. Each shoulder strap 170 has a first end portion 172 and a second end portion (not shown), both of which are coupled to the belt 110. The first end portion 172 of the shoulder strap 170 is coupled to a dorsal portion 118 of the belt 110, and the second end portion 174 of the shoulder strap 170 is coupled to a frontal portion 119 of the belt 110. In use, the shoulder straps 170 prevent the belt 110 from being pulled downwardly by the straps 130, 140, 150.

Figure 4:
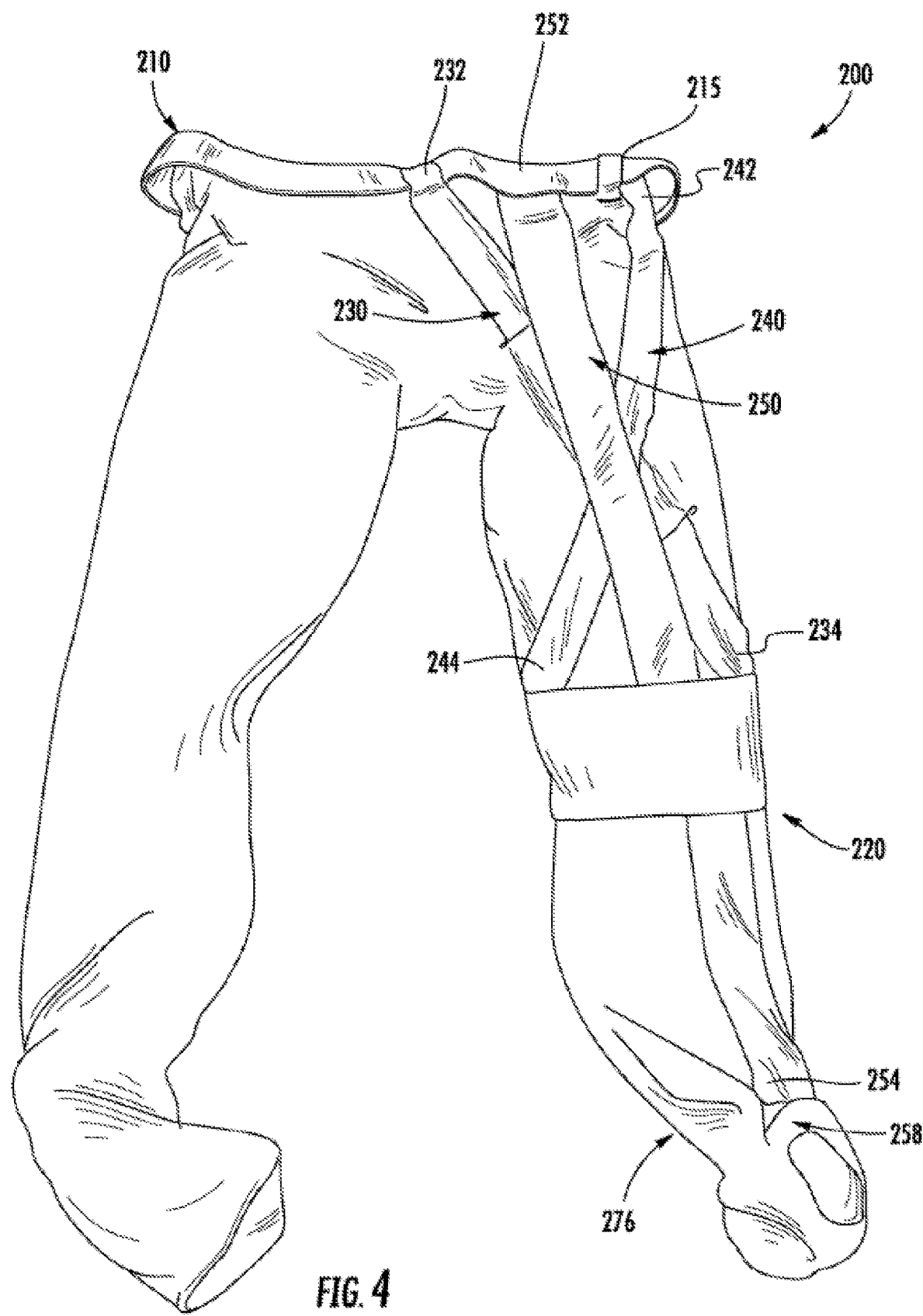
FIG. 4 is a perspective view of an assistive device for hamstring injury rehabilitation incorporated into tights in accordance with another implementation.

In an alternative implementation shown in FIG. 4, the assistive hamstring device 200 includes a pair of tights 276 into which a belt 210 and a knee sleeve 220 are incorporated. For example, the belt 210 and/or knee sleeve 220 may be formed separately from the tights 276 and directly coupled thereto, or the belt 210 and/or knee sleeve 220 may be integrally formed (e.g., woven into) the tights 276. The ankle sleeve 258 is also incorporated into the tights 276, such as is described above for the belt 210 and knee sleeve 220, but in other implementations, the ankle sleeve 258 may not be directly coupled to the tights 276 or omitted from the device 200.

The first end portions 232, 242, 252 of the straps 230, 240, 250 are sewn to the belt 210 of the tights 276, and second end portions 234, 244 of straps 230, 240 are sewn to the knee sleeve 220. The second end portion 254 of the third strap 250 is sewn to the ankle sleeve 258. In further implementations, portions of the straps 230, 240, 250 between the respective end portions may be partially or completely sewn to the tights 276. Although the straps 240, 250 in FIG. 4 are shown sewn to the tights 276, the strap 230 is shown coupled to the tights 276 using a sleeve incorporated into the fabric of the tights. However, the straps 230, 240, 250 can be coupled to the tights 276 in any of the above implementations by any means known in the art, including for example, sewn, fasteners, adhesive, or one or more sleeves or openings incorporated into the fabric of the tights.

For example, in other or further implementations, one or more sleeves are incorporated into (e.g., attached along) the tights 276 between the belt 210 and knee sleeve 220, and one or more of the straps 230, 240, 250 extend through the one or more sleeves. The one or more sleeves may also extend to a distal end of the tights or to an ankle sleeve 258. For example, the device 200 may include separate sleeves for each strap 230, 240, 250, or the device 200 may include one sleeve through which two or more straps extend. As another example, the one or more sleeves may extend a length of each strap or only a portion of the length of the strap. And, as another example, there may be multiple sleeves along a length of the strap through which the strap extends.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An assistive hamstring device, comprising:
a belt for being disposed around a waist and/or hips of a person, the belt having a first dorsal belt portion for being disposed adjacent a sagittal plane on a dorsal side of the person, a side belt portion for being disposed adjacent a coronal plane of the person, and a second dorsal belt portion disposed between the first dorsal belt portion and the side belt portion, the second dorsal belt portion for being disposed adjacent the dorsal side of the person;
a knee sleeve for being disposed around a knee of the person, the knee sleeve having a lateral knee portion for being disposed adjacent a lateral side of the knee, a medial knee portion for being disposed adjacent a medial side of the knee, and an intermediate dorsal knee portion for being disposed adjacent a dorsal portion of the knee between the lateral knee portion and the medial knee portion;
a first elastic strap having a first end portion and a second end portion, the first end portion of the first elastic strap being coupled to the first dorsal belt portion and the second end portion of the first elastic strap being coupled to the lateral knee portion;
a second elastic strap having a first end portion and a second end portion, the first end portion of the second elastic strap being coupled to the side belt portion and the second end portion of the second elastic strap being coupled to the medial knee portion; and
a third elastic strap having a first end portion, a second end portion, and an intermediate portion between the end portions and spaced apart from at least the first end portion, the first end portion of the third elastic strap being coupled to the second dorsal belt portion and the intermediate portion of the third elastic strap being coupled to the intermediate dorsal knee portion.

2. The assistive hamstring device of claim 1, wherein the first, second, and third elastic straps comprise nylon.

3. The assistive hamstring device of claim 1, further comprising an ankle sleeve for being disposed around an ankle of the person, wherein the second end portion of the third elastic strap is coupled to the ankle sleeve.

4. The assistive hamstring device of claim 1, wherein the intermediate portion and the second end portion of the third elastic strap are adjacent, and the second end portion of the third elastic strap is also coupled to the intermediate dorsal knee portion.

5. The assistive hamstring device of claim 1, further comprising a fourth strap having a first end portion coupled to the belt and a second end portion opposite the first end portion, the second end portion for being coupled to a shoulder support for being disposed on a shoulder of the person.

6. The assistive hamstring device of claim 5, wherein the shoulder support comprises shoulder pads to be worn by the person.

7. The assistive hamstring device of claim 1, further comprising at least one shoulder strap that extends over a shoulder of the person, the shoulder strap comprising a first end portion and a second end portion, the first and second end portions being coupled to the belt.

8. The assistive hamstring device of claim 7, wherein a first end portion of the shoulder strap is coupled to the dorsal portion of the belt and a second end portion of the shoulder strap is coupled to a frontal portion of the belt.

9. The assistive hamstring device of claim 1, further comprising a pair of tights, the tights comprising the belt and the knee sleeve, wherein at least a portion of each strap is coupled to the tights.

10. The assistive hamstring device of claim 9, wherein the straps are disposed within one or more sleeves defined by the tights, the one or more sleeves extending between the belt and the knee sleeve of the tights.

11. The assistive hamstring device of claim 10, wherein the end portions of the straps are sewn to the tights.

12. A method of assisting hamstring injury recovery, the method comprising:
 disposing a belt around a waist and/or hips of a person, the belt having a first dorsal belt portion disposed adjacent a sagittal plane on a dorsal side of the person, a side belt portion disposed adjacent a coronal plane of the person, and a second dorsal belt portion disposed between the first dorsal belt portion and the side belt portion, the second dorsal belt portion disposed adjacent the dorsal side of the person;
 disposing a knee sleeve around a knee of the person, the knee sleeve having a lateral knee portion disposed adjacent a lateral side of the knee, a medial knee portion disposed adjacent a medial side of the knee, and an intermediate dorsal knee portion disposed adjacent a dorsal portion of the knee between the lateral knee portion and the medial knee portion;
 coupling a first end portion of a first elastic strap to the first dorsal belt portion and a second end portion of the first elastic strap to the lateral knee portion;
 coupling a first end portion of a second elastic strap to the side belt portion and a second end portion of the second elastic strap to the medial knee portion; and
 coupling a first end portion of a third elastic strap to the second dorsal belt portion and an intermediate portion of the third elastic strap to the intermediate dorsal knee portion, wherein the intermediate portion of the third elastic strap is spaced apart from the first end portion of the third elastic strap and is between the first and second end portions of the third elastic strap.

13. The method of claim 12, wherein the first, second, and third elastic straps comprise nylon.

14. The method of claim 12, further comprising disposing an ankle sleeve around an ankle of the person, wherein the second end portion of the third elastic strap is coupled to the ankle sleeve.

15. The method of claim 12, wherein the intermediate portion and the second end portion of the third elastic strap are adjacent each other, and the second end portion of the third elastic strap is also coupled to the knee sleeve.

16. The method of claim 12, further comprising coupling a first end portion of a fourth strap to the belt and a second end portion of the fourth strap to a shoulder support disposed on a shoulder of the person.

17. The method of claim 16, wherein the shoulder support comprises shoulder pads worn by the person.

18. The method of claim 12, further comprising disposing at least one shoulder strap over a shoulder of the person, the shoulder strap having a first end portion and second end portion, and the first and second end portions of the shoulder strap being coupled to the belt.

19. The method of claim 18, wherein the first end portion of the shoulder strap is coupled to the dorsal portion of the belt and the second end portion of the shoulder strap is coupled to a frontal portion of the belt.

20. The method of claim 12, wherein disposing the belt around the waist and/or hips and disposing the knee sleeve around the knee comprises donning a pair of tights into which the belt and knee sleeve are incorporated and to which at least a portion of the straps are coupled.

21. The method of claim 20, wherein the tights define one or more sleeves and the straps are disposed within the one or more sleeves.

22. The method of claim 20, wherein coupling end portions of the straps to the tights comprises sewing the end portions of the straps to the tights.

23. The method of claim 12, wherein coupling respective end portions of the first, second, and third straps to the belt comprises sewing the respective end portions of the first, second, and third straps to the belt, and coupling respective end portions of the first and second straps to the knee sleeve comprises sewing the respective end portions of the first and second straps to the knee sleeve.

* * * * *